(12) United States Patent
Copf

(10) Patent No.: US 6,193,760 B1
(45) Date of Patent: Feb. 27, 2001

(54) THIGH PROSTHESIS

(76) Inventor: Franz Copf, Marienstrasse 12, D-70178 Stuttgart (DE)

(*) Notice: Subject to any disclaimer, the term of this patent is extended or adjusted under 35 U.S.C. 154(b) by 0 days.

(21) Appl. No.: 09/154,550

(22) Filed: Sep. 16, 1998

(30) Foreign Application Priority Data

Sep. 16, 1997 (DE) .............................. 197 40 689

(51) Int. Cl.[7] .................................................. A61F 2/36
(52) U.S. Cl. ....................................................... 623/23.35
(58) Field of Search ........................... 623/22, 23, 23.15, 623/23.18, 23.35

(56) References Cited

U.S. PATENT DOCUMENTS

| | | | |
|---|---|---|---|
| 4,435,854 | * | 3/1984 | Keller ...................... 623/23 |
| 4,546,501 | * | 10/1985 | Gustilo ..................... 623/23 |
| 4,608,053 | * | 8/1986 | Keller ...................... 623/23 |
| 4,713,076 | * | 12/1987 | Draenert ................... 623/23 |
| 4,738,681 | * | 4/1988 | Koeneman ................. 623/23 |
| 4,743,263 | * | 5/1988 | Petrtyl ..................... 623/23 |
| 4,808,186 | * | 2/1989 | Smith ...................... 623/23 |
| 4,978,359 | * | 12/1990 | Wilhelm ................... 623/23 |
| 5,002,579 | | 3/1991 | Copf et al. . |
| 5,032,130 | * | 7/1991 | Schelhas ................... 623/23 |
| 5,507,829 | * | 4/1996 | Thongpreda ............... 623/23 |
| 5,897,592 | * | 4/1999 | Caldarise .................. 623/22 |

* cited by examiner

Primary Examiner—Michael J. Milano

(57) ABSTRACT

A prosthesis element for a thigh prosthesis has a shaft which can be inserted into the upper end of a femur. The upper end of the shaft carries an inclined transverse support plate and a support post onto which a condyle can be fitted. The shaft has an upper proximal shaft section and a lower distal shaft section. These two shaft sections are tilted relative to one another to an acute angle. The shaft sections have substantially rectangular cross section and taper to the distal end of the shaft. One of the shaft sections comprises a lower section, which is twisted about the longitudinal axis of this shaft section.

19 Claims, 4 Drawing Sheets

THIGH PROSTHESIS

The invention relates to a thigh prosthesis and more particularly, to a thigh prosthesis with a shaft that can be inserted into the upper end of a femur.

DISCUSSION OF RELEVANT ART

A thigh prosthesis of this type is disclosed in DE 36 15 655A, corresponding to U.S. Pat. No. 5,002,579. It comprises an anchoring shaft formed by anchoring pillars suspended from the support plate. The anchoring pillars each support a plurality of axially successive annular anchoring collars. Spongiosa can grow into the intermediate spaces between the individual anchoring pillars. In this manner, the prosthesis is securely connected to the femur following healing without the use of cement.

In order to adapt the prosthesis to differently sized cavities in the proximal end of the femur, free ends of anchoring pillars can be shortened as required. However, this can only be effected without difficulty in the case of anchoring pillars which end freely or are unattached. In the case of anchoring pillars which are connected to one another, a separation of parts of the cage structure would be associated with such an intensive intervention into the mechanical support structure with consequences which could not be overlooked by the surgeons, that the durability and loading capacity of the prosthesis could no longer be guaranteed. Also in the case of shaft prostheses which are connected to the corticalis of the femur using cement, it is clearly difficult to obtain an improved adaptation to the bone geometry by mechanical reworking of the prosthesis during the course of the operation. However, it is particularly desirable in the case of cemented prostheses that the cement layer does not vary locally to an excessive degree, which means that the anchoring section must closely match the bone geometry at the stage of manufacture.

By way of the present invention, a thigh prosthesis according to the field of invention is therefore to be further developed in such a manner that it more closely matches the geometry of the corticalis in the upper end shaft of the femur without mechanical reworking.

SUMMARY OF THE INVENTION

This object is attained according to the invention by a thigh prosthesis having the following features.

It is recognised that the geometry of the corticalis in the upper end section of the femur can generally be better taken into account by constructing the shaft of the prosthesis from two shaft sections which are tilted relative to one another.

Using a set of prostheses which differ between the two shaft sections in respect of the bending angle but which otherwise have the same dimensions, it is possible to take into account a very large number of different implantation conditions.

Consequently, it is no longer necessary to compensate the misfitting of the prosthesis external surface and the internal surface of the corticalis by means of cement layers of a thickness which varies greatly locally.

Advantageous developments of the invention are laid out in the subclaims.

Advantageously, the acute angle (b) measures between 5° and 30°, preferably between 10° and 20°. The angles given are most suitable for the most commonly occurring thigh geometries. If the bending angle in a prosthesis set is graded in stages of 5°, then there is always one prosthesis in the set which is well adapted to the geometry of the upper end of the thigh with only slight residual thickness variations in the cement layer.

Advantageously, the line of intersection between the main surfaces of the two shaft sections lies at a distance of between 50 and 70% of the overall length of the shaft, preferably approximately 60% of the overall length of the shaft from the free end of the distal shaft section. This gives preferred values for the distance of the shaft bending site from the distal end of the shaft. Again, prostheses can be provided in a prosthesis set in which the shaft bending line lies at different distances from the distal end of the shaft, the grading preferably being effected in stages of 5 mm.

Advantageously, the support plate extends in a plane lying substantially perpendicular to the proximal axis (P). In a thigh prosthesis according to this feature, the support plate extends substantially in the horizontal direction when the prosthesis is implanted.

Advantageously, the support plate projects in the circumferential direction substantially uniformly beyond the proximal end of the proximal shaft section. In a thigh prosthesis according to this feature, the edge of the support plate can form a substantially flush continuation of the external surface of the proximal end of the corticalis. The support plate can then form a lid, by means of which the upper end of the femur, which is open following resectioning, is sealed again.

Advantageously, the shaft sections comprise a non-circular, preferably substantially rectangular cross section, taper in the direction from proximal to distal and at least one shaft section comprises a lower section, which is twisted about the longitudinal axis of the shaft section in question. With the cross sectional shape for the shaft sections according to this feature, it is possible to attain a particularly good adaptation to the transverse cross section of the cavity, which is obtained by removing spongiosa from the upper end section of the femur. In this respect, the torsion also disclosed in claim 6 of at least one lower section of at least one of the shaft sections allows for particularly good adaptation to the internal surface of the corticalis.

Advantageously, the angle of torsion of the lower section in question measures between 5 and 30°, preferably between 10 and 15°, a lower section of the proximal shaft section again being preferably twisted through a smaller angle than a lower section of the distal shaft section. Preferred torsion angles used for a shaft section lower section of this type are given by these features.

Advantageously, the shaft sections comprise a substantially smooth, continuous surface. The development of the invention according to this feature is also advantageous in that the cement layer between the external surface of the shaft and the internal surface of the corticalis has a substantially constant thickness.

Advantageously, the surfaces of the shaft sections and preferably, also of the support plate comprise microirregularities produced by sandblasting, which are preferably additionally etched. With the development of the invention according to this feature, it is attained that the cement used for the implantation adheres particularly well to the outside of the shaft.

Advantageously, laterally the support plate comprises a raised lateral smooth section, whose plane preferably forms an angle of 100° to 150° with the main section of the support plate. As a result of the development of the invention according to this feature, it is possible to merely partially resection the greater trochanter of the femur, which can therefore be partially left in place. This is advantageous with a view towards a good transmission of transverse forces from the prosthesis to the corticalis.

Advantageously, the element is a forged element or cast element or biocompatible material, more particularly titanium. The development of the invention according to this feature is advantageous with a view towards high mechanical loadability of the prosthesis and with a view towards low manufacturing costs.

BRIEF DESCRIPTION OF THE DRAWINGS

The invention will be explained in further detail in the following with the aid of an embodiment with reference to the attached drawings, in which.

DETAILED DESCRIPTION OF THE PREFERRED EMBODIMENTS

Figure 1:
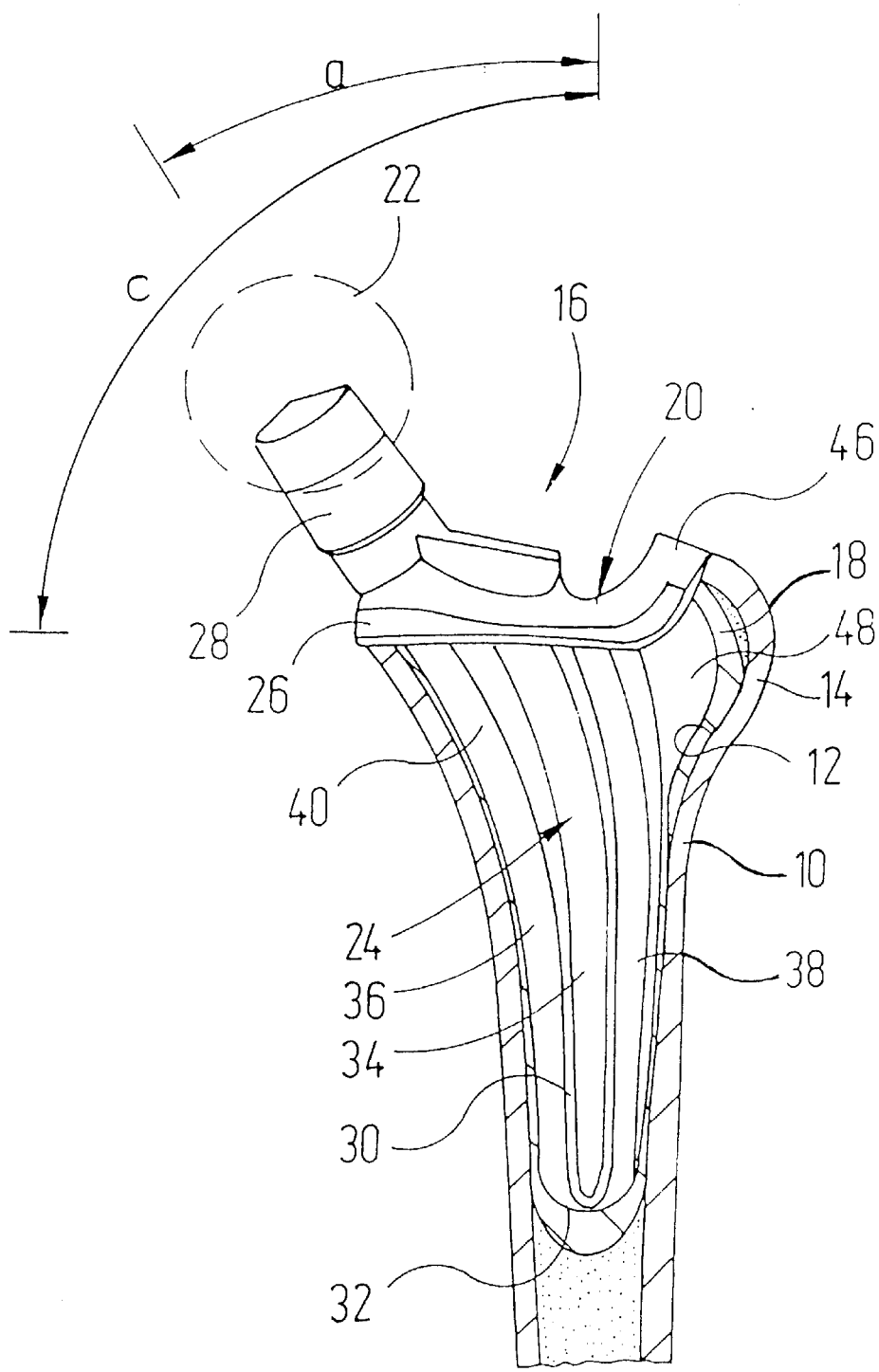
FIG. 1: is a view of a thigh prosthesis taken in the direction from ventral to dorsal, a condyle and an upper section of a femur in which the prosthesis is implanted being schematically indicated.
Figure 1:
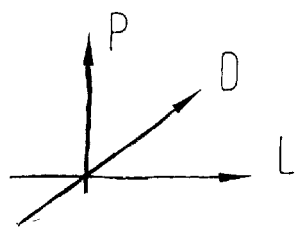

In the drawings, the reference 10 designated the proximal part of a femur. The minor trochanter and the condyle supported thereby have been resectioned, the resectioning line extending substantially in the horizontal direction. An end section of the resectioning line lying to the right in FIG. 1 is upwardly inclined, so that a part of the greater trochanter is retained.

The spongiosa is removed from the upper end section of the femur 10, so that a cavity 12 is formed, which is defined by the internal surface of the remaining corticalis 14.

A prosthesis 16 is fixedly inserted into the cavity 12 by means of a cement layer 20. The prosthesis 16 is formed by a prosthesis element 18 forged from titanium, which will be described in detail below, and a condyle made of ceramic material with a polished surface which is supported by the prosthesis element 20.

The prosthesis element 20 comprises three main elements, namely a shaft 24 lying in the cavity 12, a support plate 26 covering the upper end of the resectioned corticalis 14 in a substantially flush manner and a support post 28, which is supported by the support plate 26 and to which the condyle 22 is fitted.

In order to describe the geometry of the prosthesis element 20, coordinates specific to the prosthesis element are used in the following and in the claims. In this respect, the plane of the drawing of FIG. 1 is used as a basis, which represents a very rough approximation of a sort of median plane of the prosthesis element. For these reasons, the term main plane is selected for this plane.

The longitudinal axis of the lowermost end section of the shaft 24, which lies in the main plane, is referred to in the following as the proximal axis. In FIG. 1, it extends from the bottom to the top, i.e. from distal to proximal in relation to the end of the femur. This axis is marked P in the drawing. A further axis, which extends from left to right in the drawing, i.e. from medial to lateral in relation to the femur end, is referred to in the following as the lateral axis and is marked L in the drawing. The third axis of the Cartesian coodinate system used to describe the geometry of the prosthesis element 20 extends perpendicular to the plane of the drawing of FIG. 1, i.e. from ventral to dorsal. This axis is referred to in the following as the D-axis and bears the reference D. The main plane thus corresponds to the L-P plane.

The correlation between the above-mentioned prosthesis coordinates and the so-called physiological longitudinal axis (PLA) of the (overall) thigh bone is as follows: The PLA substantially coincides with the P-axis. In the PL plane (plane of drawing in FIG. 1), the projection of PLA is tilted clockwise through 1.2° relative to the P-axis. In the PD plane (plane of drawing in FIG. 2), the projection of the PLA is tilted clockwise through 3.5° relative to the P-axis.

As is clear from the drawings, the shaft 24 has a distal shaft section 30 with a rounded end face 32.

The shaft section 30 has a substantially rectangular transverse cross section, the narrow sides of the rectangle (extending perpendicular to the plane of the drawing) being rounded and the longitudinal surfaces of the rectangle each presenting a flat recess 34. The recess 34 is therefore defined by bead-like ribs 36, 38 extending along the edges of the shaft 24. The cross section of the distal shaft section 30 increases continuously in the proximal direction, i.e. from the bottom towards the top in the drawing. The external surfaces of the distal shaft section thus form an approximate pyramid, whose generating angle viewed in the dorsal direction (i.e. in the main plane) is approximately 10°. In its uppermost end section, a proximal shaft section 40 of the shaft 24 extends parallel to the axis of the support post 28. The axis of the support post 28 forms an angle a, which is approximately 35°, with the proximal axis.

Figure 2:
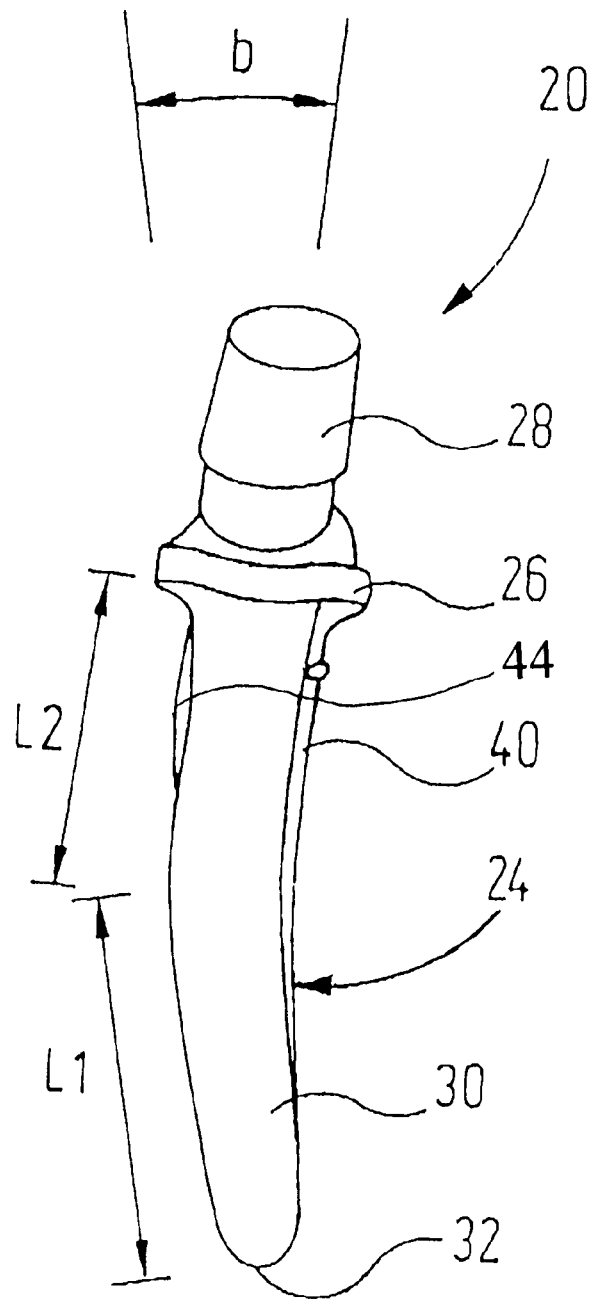
FIG. 2 is a view of the prosthesis shown in FIG. 1 in the direction from medial to lateral, i.e. from left to right in FIG. 1.
Figure 2:
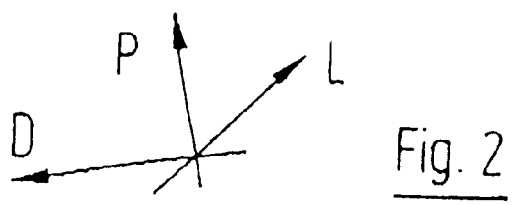
Figure 3:
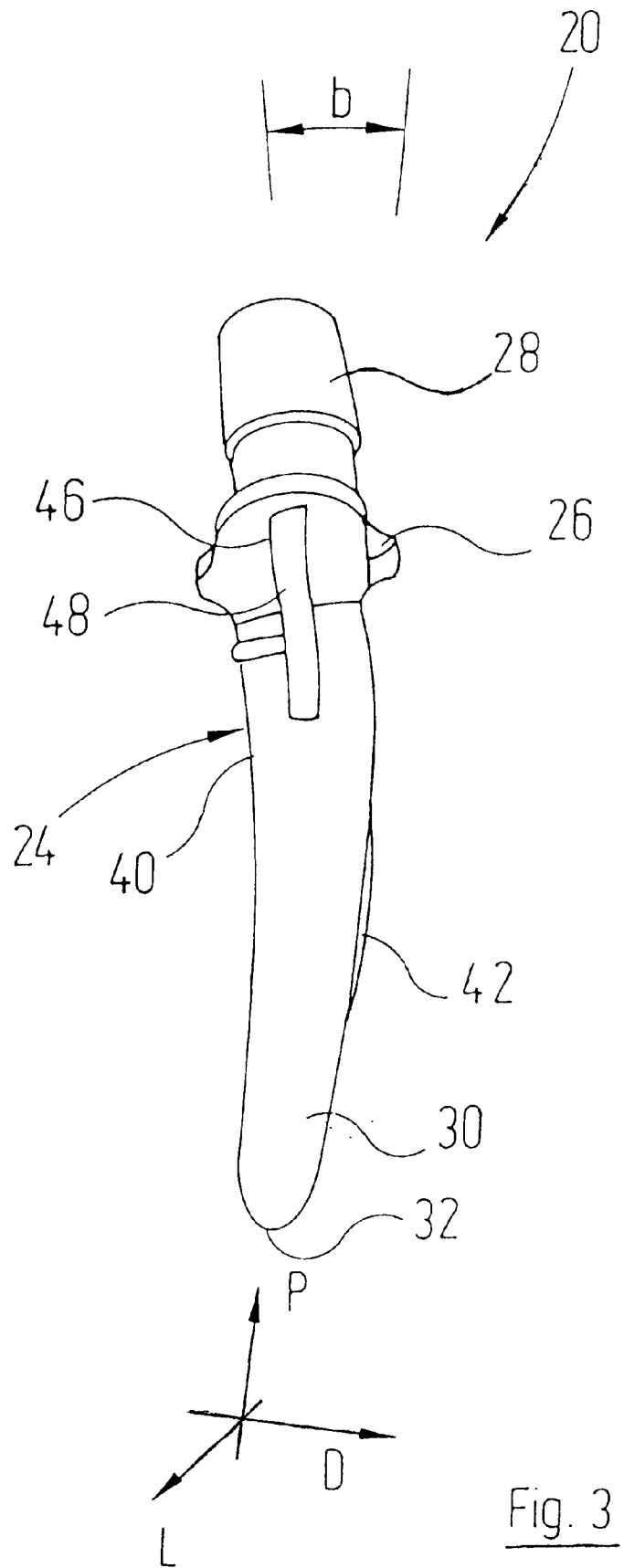
FIG. 3 is a view of the prosthesis according to FIG. 1 in the direction from lateral to medial, i.e. from right to left in FIG. 1.

As is particularly visible from FIG. 2, the axis of the support post 28 and of the upper end section of the proximal shaft section 40 is additionally tilted through a second angle b in the ventral direction out of the L-P plane defined by the distal shaft section 30. The angle b measures approximately 15° in the illustrated embodiment.

In the illustrated embodiment, the bending line between the distal shaft section 30 and the proximal shaft section 40 lies at a distance $l_1$ of approximately 45 mm from the distal end of the shaft 24. The distance $l_2$ between the bending line and the support plate 26 measures approximately 35 mm.

The angle of pitch c between the plane of the support plate 26 and the P-axis (cf. FIG. 1) measures 87°. Viewed perpendicular to the PD-plane (plane of drawing of FIG. 2), the support plate 26 lies perpendicularly on the proximal shaft section 40.

The implantation geometries which are predominantly found in practice can be taken into account by providing three angle variants and three bending line variants for each overall length of the shaft section, i.e. a total of nine different prostheses. In this respect, an average bending angle of approximately 15° and a somewhat smaller bending angle of 10° and a somewhat larger bending angle of 20° are selected. The position of the median line is selected upwards from the distal end at a location lying approximately at the 60% mark of the overall length of the shaft or 5 mm offset from this site towards the distal or proximal end.

Figure 4:
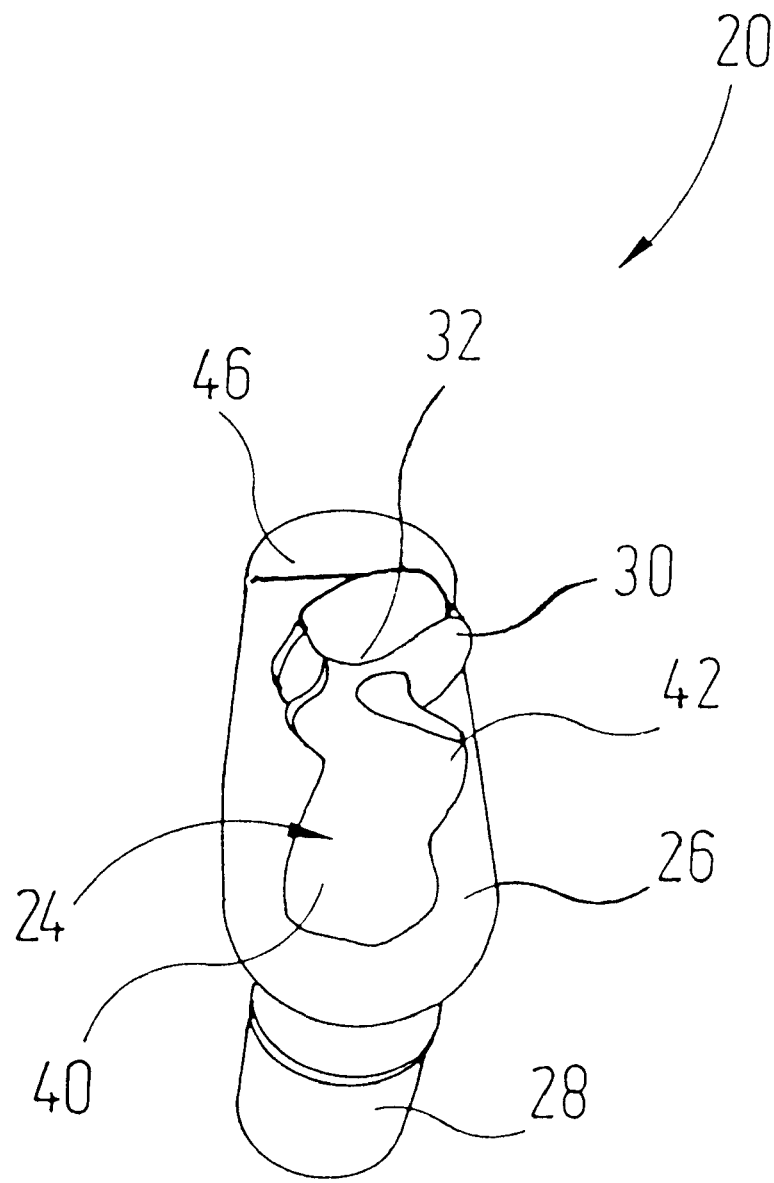
FIG. 4 is a view of the prosthesis according to FIG. 1 in the direction from distal to proximal, i.e. from below in FIG. 1.

As particularly visible from FIG. 4, the distal shaft section 30 has a twisted lower section 42 which is rotated out of its plane. In FIG. 2, the lower section 44 of the proximal shaft section 40 can be seen, which is rotated out of its plane.

These twisted lower sections again allow for improved adaptation of the external surface of the shaft 24 to the internal surface of the corticalis 14. The torsion angle of the lower section 42 about the P-axis is approximately 30°, the torsion angle of the lower section 44 about the axis of the proximal shaft section 40 approximately 15°.

The support plate 26 has a lateral side section 46, which rises towards the edge of the corticalis 14 lying in the minor trochanter. A flap 48 lying in the main surface of the proximal shaft section and extending from the distal boundary surface of the support plate 26 to the lateral side face of the shaft section 40, joins the corticalis 14 of the upper bone end.

The prosthesis element 18 is manufactured by forging a blank in a die. Following forging, the surface is roughened by sandblasting and then etched. In this manner, micro-irregularities are obtained on the prosthesis surface, which are sharp-edged and to which the cement layer 18 can grip so as to provide good adhesion.

The invention has been described above with reference to a cemented prosthesis. However, it goes without saying that the geometries detailed above can also be provided in like manner in prostheses which can be implanted without cement and in which the shaft forms an open cage structure.

It is also understood that the application of the invention is not restricted to prostheses forged from metal, more particularly titanium or steel, but can also be used in cast prostheses or sinter prostheses or even in prostheses made of other materials, e.g. ceramic material.

What is claimed is:

1. A prosthesis element for a thigh prosthesis with a shaft (24), which can be inserted into the upper end of a femur, with an inclined transverse support plate (26), which is fitted to the upper end of the shaft (24) and projects beyond the upper end of the shaft (24) on all sides, and with a support post (28) inclined in the medial direction, which is supported by the support plate (26) and onto which a condyle (22) can be fitted, wherein the shaft (24) comprises an upper, proximal shaft section (40) and a lower, distal shaft section (30), the main surfaces of these two shaft sections (30, 40) being tilted relative to one another through an acute angle (b) in such a manner that the line of intersection between the two main surfaces of the two shaft section (30, 40) extends substantially in the lateral direction wherein the shaft section (30, 40) comprise a non-circular cross-sections, taper in the direction from proximal to distal and at least one shaft section comprises a lower section (42, 44) that is twisted about the longitudinal axis of the at least one shaft section.

2. A prosthesis element as claimed in claim 1, wherein the acute angle (b) measures between 5° and 30°.

3. A prosthesis element as claimed in claim 1, wherein the line of intersection between the main surfaces of the two shaft sections (40, 30) lies at a distance of between 50 and 70% of the overall length of the shaft.

4. A prosthesis element as claimed in claim 1, wherein the support plate (26) extends in a plane lying substantially perpendicular to the proximal axis (P).

5. A prosthesis element as claimed in claim 1, wherein the support plate (26) projects in the circumferential direction substantially uniformly beyond the proximal end of the proximal shaft section (40).

6. A prosthesis element as claimed in claim 1, wherein the shaft sections (24, 40) are of substantially rectangular cross section.

7. A prosthesis element as claimed in claim 6, wherein the angle of the torsion of the lower section (42, 44) about the axis of the shaft section (42, 44) in question measures between 5 and 30°.

8. A prosthesis element as claimed in claim 1, wherein the shaft sections (30, 40) comprise a substantially smooth, continuous surface.

9. A prosthesis element as claimed in one of claims 1 to 8, wherein the surfaces of the shaft sections (30, 40) comprise micro-irregularities produced by sandblasting.

10. A prosthesis element as claimed in one of claimed 1 to 9, wherein laterally the support plate (26) comprises a raised lateral smooth section (46).

11. A prosthesis element as claimed in one of claims 1 to 10, wherein said element is forged element or cast element of bicompatible material.

12. A prosthesis element as claimed in claim 2, wherein the acute angle (b) measures between 10° and 20°.

13. A prosthesis element as claimed in claim 3, wherein the two shaft section (40, 30) lies at a distance of approximately 60% of the overall length of the shaft, from the free end of the distal shaft section (30).

14. A prosthesis element as claimed in claim 7, wherein the anlge of torsion of the lower section (42, 44) about the axis of the shaft section (42, 44) in question measures between 10 and 15°.

15. A prosthesis element as claimed in claim 7, wherein a lower section (44) of the proximal shaft section (40) again being twisted through a smooth angle than a lower section (42) of the distal shaft section (30).

16. A prosthesis element as claimed in claim 9, wherein the support plate (26) comprises micro-irregularities produced by sand-blasting.

17. A prosthesis element as claimed in claim 9, wherein the surfaces of the shaft sections (30, 40) are additionally etched.

18. A prosthesis element as claimed in claim 10, wherein the plane of the raised lateral smooth section forms an angle of 100° to 150° with the main section of the support plate (26).

19. A prosthesis element as claimed in claim 11, wherein said bicompatible material comprises titanium.

* * * * *